(12) United States Patent
Narula et al.

(10) Patent No.: US 7,678,748 B2
(45) Date of Patent: *Mar. 16, 2010

(54) ORGANOLEPTIC COMPOUNDS AND THEIR USE IN PERFUME COMPOSITIONS

(75) Inventors: Anubhav P. S. Narula, Hazlet, NJ (US); Edward Mark Arruda, Cliffwood, NJ (US); Franc T. Schiet, Naarden (NL)

(73) Assignee: International Flavors & Fragrances Inc., New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/268,476

(22) Filed: Nov. 11, 2008

(65) Prior Publication Data

US 2009/0068137 A1    Mar. 12, 2009

Related U.S. Application Data

(60) Division of application No. 11/457,244, filed on Jul. 13, 2006, now Pat. No. 7,485,606, which is a continuation-in-part of application No. 11/298,117, filed on Dec. 9, 2005, now Pat. No. 7,172,994.

(51) Int. Cl.
*C11D 3/50* (2006.01)
(52) U.S. Cl. .............................. 510/102; 512/8; 568/579
(58) Field of Classification Search .................... 512/8; 568/700
See application file for complete search history.

(56) References Cited

U.S. PATENT DOCUMENTS 5,113,021 A * 5/1992 Frater et al. .................. 568/341

OTHER PUBLICATIONS

L. Skattebol et al., Journal of Agricultural and Food Chemistry 2004, vol. 52, issue 23, pp. 6944-6949 (abstract). Oct. 2004.*

* cited by examiner

*Primary Examiner*—John R Hardee
(74) *Attorney, Agent, or Firm*—Elizabeth M. Quirk; XuFan Tseng; Joseph F. Leightner

(57) ABSTRACT

The present invention is directed to novel compounds which possess unique organoleptic properties containing the following general formula:

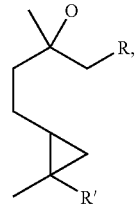

wherein R and R' each independently represents hydrogen or a $C_1$-$C_7$ moiety, and the use of these compounds as fragrance materials to enhance fragrance formulations in perfumes, toilet waters, colognes, fabric care products, personal products, and the like.

14 Claims, No Drawings

ORGANOLEPTIC COMPOUNDS AND THEIR USE IN PERFUME COMPOSITIONS

STATUS OF RELATED APPLICATIONS

This application is a divisional of U.S. Ser. No. 11/457,244, filed Jul. 13, 2006, now U.S. Pat. No. 7,484,606, which is a continuation-in-part of U.S. Ser. No. 11/298,117, filed Dec. 9, 2005, now U.S. Pat. No. 7,172,994, each of which is hereby incorporated by reference in its entirety.

FIELD OF THE INVENTION

The present invention relates to new chemical entities and the incorporation and use of the new chemical entities as fragrance materials.

BACKGROUND OF THE INVENTION

There is an ongoing need in the fragrance industry to provide new chemicals to give perfumers and other persons the ability to create new fragrances for perfumes, colognes and personal care products. Those with skill in the art appreciate how differences in the chemical structure of the molecule can result in significant differences in the odor, notes and characteristics of a molecule. These variations and the ongoing need to discover and use the new chemicals in the development of new fragrances allows perfumers to apply the new compounds in creating new fragrances.

SUMMARY OF THE INVENTION

The present invention provides novel chemicals, and the use of the chemicals to enhance the fragrance of perfumes, toilet waters, colognes, personal products and the like. In addition, the present invention is directed to the use of the novel chemicals to enhance fragrance in perfumes, toilet waters, colognes, personal products and the like.

More specifically, the present invention is directed to the novel compounds, represented by Formulas I-III set forth below:

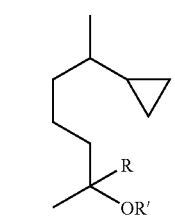

Formula I

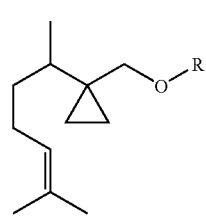

Formula II

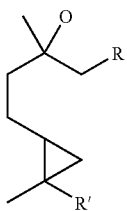

Formula III wherein R and R' each independently represents hydrogen or a $C_1$-$C_7$ moiety, and the use of these materials as a fragrance chemical to enhance fragrance in perfumes, toilet waters, colognes, personal products and the like.

Another embodiment of the invention is a method for enhancing a perfume composition by incorporating an olfactory acceptable amount of the compounds provided above.

These and other embodiments of the present invention will be apparent by reading the following specification.

DETAILED DESCRIPTION OF THE INVENTION

In Formulas I, II and III above, wherein R and R' each independently represents hydrogen or a $C_1$-$C_7$ moiety. Representative $C_1$-$C_7$ moieties include alkyl groups such as but not limited to $CH_3$, $C_2H_5$, $C_3H_7$, $C_4H_9$, $C_5H_{11}$, $CH(CH_3)$ $CH_2CH_2CH_3$, $CH_2CH(CH_3)CH_2CH_3$ and $CH_2CH_2CH(CH_3)$ $CH_3$, cyclopropyl, cyclobutyl, cyclopentyl; as well as unsaturated moieties including but not limited to $CH=CHCH_2CH_2CH_3$, $CH_2CH=CHCH_2CH_3$, $CH_2CH_2$ $CH=CHCH_3$, and $CH=C(CH_3)CH_2CH_3$. Those with skill in the art will appreciate that the present invention includes various isomers including chiral or optically active isomers, which are contemplated within the scope of the present invention.

In the preferred embodiment of the invention, the novel compounds of the present invention are represented by the following structures:

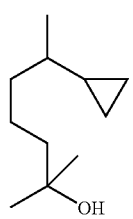

Structure I

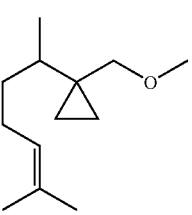

Structure II

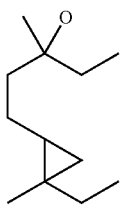

Structure III

Those with the skill in the art will appreciate that the compound of Structure I is cyclopropanepentanol, alpha,alpha,epsilon-trimethyl-; the compound of Structure II is cyclopropane, 1-(1,5-dimethyl-4-hexenyl)-1-(methoxymethyl)-; and the compound of Structure III is cyclopropanepropanol, alpha, 2-diethyl-alpha, 2-dimethyl.

Structure I is described as having fresh strong, citrus, lime and herbal fragrance notes. Structure II has strong, citrus, rosy and floral fragrance notes. Structure III has refreshingly light, clean, floral, citrus, lemon, orange and sweet fragrance notes.

The compounds of the present invention may be prepared from the corresponding starting materials by the following sequences using the Yamamoto and Simmon-Smith cyclopropanation reactions:

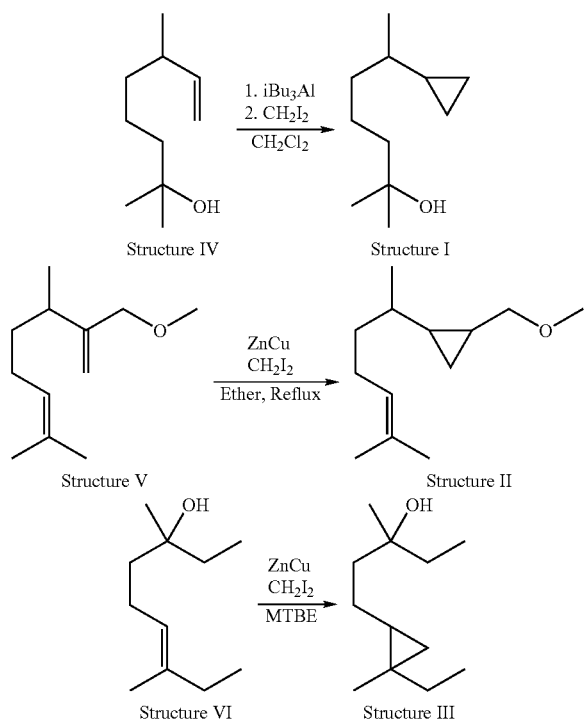

Those with skill in the art will recognize that some of the compounds of the present invention have a number of chiral centers, thereby providing numerous isomers of the claimed compounds. It is intended herein that the compounds described herein include isomeric mixtures of such compounds, as well as those isomers that may be separated using techniques known to those having skill in the art. Suitable techniques include chromatography such as HPLC, and particularly gel chromatography and solid phase microextraction ("SPME").

We have surprisingly discovered that the compounds of Formulas I-III are well suited for use as fragrance ingredients.

The use of the compounds of the present invention is widely applicable in current perfumery products, including the preparation of perfumes and colognes, the perfuming of personal care products such as soaps, shower gels, and hair care products as well as air fresheners and cosmetic preparations. The present invention can also be used to fabric care products and perfume cleaning agents, such as, but not limited to detergents, dishwashing materials, scrubbing compositions, window cleaners and the like.

In these preparations, the compounds of the present invention can be used alone or in combination with other perfuming compositions, solvents, adjuvants and the like. The nature and variety of the other ingredients that can also be employed are known to those with skill in the art.

Many types of fragrances can be employed in the present invention, the only limitation being the compatibility with the other components being employed. Suitable fragrances include but are not limited to fruits such as almond, apple, cherry, grape, pear, pineapple, orange, strawberry, raspberry; musk, flower scents such as lavender-like, rose-like, iris-like, carnation-like. Other pleasant scents include herbal and woodland scents derived from pine, spruce and other forest smells. Fragrances may also be derived from various oils, such as essential oils, or from plant materials such as peppermint, spearmint and the like.

A list of suitable fragrances is provided in U.S. Pat. No. 4,534,891, the contents of which are incorporated by reference as if set forth in its entirety. Another source of suitable fragrances is found in Perfumes, Cosmetics and Soaps, Second Edition, edited by W. A. Poucher, 1959. Among the fragrances provided in this treatise are acacia, cassie, chypre, cyclamen, fern, gardenia, hawthorn, heliotrope, honeysuckle, hyacinth, jasmine, lilac, lily, magnolia, mimosa, narcissus, freshly-cut hay, orange blossom, orchid, reseda, sweet pea, trefle, tuberose, vanilla, violet, wallflower, and the like.

Olfactory effective amount is understood to mean the amount of compound in perfume compositions the individual component will contribute to its particular olfactory characteristics, but the olfactory effect of the perfume composition will be the sum of the effects of each of the perfumes or fragrance ingredients. Thus the compounds of the invention can be used to alter the aroma characteristics of the perfume composition, or by modifying the olfactory reaction contributed by another ingredient in the composition. The amount will vary depending on many factors including other ingredients, their relative amounts and the effect that is desired.

The level of the compounds of the present invention employed in a perfumed article varies from about 0.005 to about 10 weight percent, preferably from about 0.5 to about 8, and more preferably from about 1 to about 7 weight percent. In addition to the compounds other agents can be used in conjunction with the fragrance. Well known materials such as surfactants, emulsifiers, polymers to encapsulate the fragrance can also be employed without departing from the scope of the present invention.

Another method of reporting the level of the compounds of the invention in the perfumed composition, i.e., the compounds as a weight percentage of the materials added to impart the desired fragrance. The compounds of the invention can range widely from 0.005 to about 70 weight percent of the perfumed composition, preferably from about 0.1 to about 50, and more preferably from about 0.2 to about 25 weight percent. Those with skill in the art will be able to employ the desired level of the compounds of the invention to provide the desired fragrance and intensity.

The following are provided as specific embodiments of the present invention. Other modifications of this invention will be readily apparent to those skilled in the art. Such modifications are understood to be within the scope of this invention. As used herein all percentages are weight percent unless otherwise noted, ppm is understood to stand for parts per million and g is understood to be grams. IFF as used in the examples is understood to mean International Flavors & Fragrances Inc., New York, N.Y., USA.

EXAMPLE A

Preparation of Cyclopropanepentanol, Alpha, Alpha, Epsilon,Trimethyl

To a dry 500 ml multi-neck round bottom flask fitted with an air stirrer, nitrogen inlet condenser and an addition funnel 62 g of 99% optically pure DH Myrecerol (commercially available at IFF) and 1000 ml Methylene Chloride were charged in a pot, flame dried, and cooled to 10° C. The mixture was heated ant maintained at 60° C. Eighty hundred (800) ml of triisobutyl aluminum was charged in a clean dry cannula. The reaction mixture was aged for 7.5 hours, and quenched with saturated $NH_4Cl$. The aqueous layer was separated and the organic layer was washed with 200 ml of water. The organic layer was then dried over anhydrous $MgSO_4$, and the final product was recovered with a 70% yield.

$^1$H NMR: 0.1 ppm (m, 1H); 0.3-0.5 ppm (m, 3H); 0.7 ppm (s, 1H); 1.0 ppm (d, 3H); 1.2 ppm (s, 7H); 1.3 ppm (m, 1H); 1.4 ppm (m, 5H).

The compound was described as having fresh, strong, citrus, lime and herbal fragrance notes.

EXAMPLE B

Preparation of Cyclopropane 1-(1,5-Dimethyl-4-Hexenyl)-1-(Methoxymethyl)

To a dry 100 ml multi-neck round bottom flask fitted with an air stirrer, nitrogen inlet condenser and an addition funnel 22 g of ether, 7.5 g of zinc copper (ZnCu), 26.8 g methylene iodide ($CH_2I_2$), and 31 ml of ether were added and stirred. The mixture was heated and maintained at 60° C. The mixture was refluxed at 35° C. overnight and the final product was recovered in 70% yield.

$^1$H NMR: 0.5 ppm (m, 4H); 1.0 ppm (s, 4H); 1.3 ppm (s, 1H); 1.5 ppm (d, 3H); 1.7 ppm (s, 3H); 1.8 ppm (s, 3H); 2.0 ppm (m, 2H); 3.2 ppm (m, 2H); 3.4 ppm (m, 3H); 5.1 ppm (s, 1H).

The compound was described as having strong citrus, floral and rosy fragrance notes.

EXAMPLE C

Preparation of Cyclopropanepropanol, Alpha, 2-Diethyl-Alpha,2-Dimethyl

To a dry 100 ml multi-neck round bottom flask fitted with an air stirrer, nitrogen inlet condenser and an addition funnel 0.22 mole of ZnCu, 0.2 mole of $CH_2I_2$, 200 ml of MTBE, and 3 crystals of $I_2$ were charged and stirred. 0.10 mole of D.H. Ethyl linanlool was added dropwise and the sample was aged at room temperature. The reaction mixture was quenched with 200 ml of saturated $NH_4Cl$ solution, the aqueous phase was separated and the final product was recovered with a 70% yield.

$^1$H NMR: 0.4 ppm (m, 1H); 0.5 ppm (m, 1H); 0.9 ppm (m, 2H); 1.0 ppm (m, 6H); 1.2 ppm (m, 1H); 1.4 ppm (m, 3H); 1.6 ppm (m, 2H); 1.7 ppm (m, 2H); 1.8 ppm (m, 2H) 2.0 ppm (m, 2H); 2.1 ppm (m, 1H).

The compound was described as having refreshingly light, clean, floral, citrus, lemon, orange and sweet fragrance notes.

EXAMPLE D

Demonstration Formula (Shower Gel) with Cyclopropanated Dihydro Myrcenol

| Ingredients | Parts |
| --- | --- |
| Aldehyde AA Triplal | 15.00 |
| Benzophenone | 5.00 |
| Bergamot Oil | 100.00 |
| Cardamom Oil | 8.00 |
| Cyclopropanated Dihydro Myrcenol | 60.00 |
| Diphenyl Oxide | 10.00 |
| Galaxolide | 100.00 |
| Geranium Oil | 12.00 |
| Hedione | 60.00 |
| Helional | 6.00 |
| Lilial | 100.00 |
| Lyral | 50.00 |
| Melafleur | 12.00 |
| Menthol | 37.00 |
| Nerol | 45.00 |
| Patchouli Oil | 15.00 |
| Peppermint Oil | 40.00 |
| Phenyl Ethyl Alcohol | 125.00 |
| Spearmint Oil | 200.00 |
| Total Weight | 1000.00 |

The addition of Cyclopropanated Dihydro Myrcenol to the fragrance formulation of the shower gel lifts the fragrance and enhances the naturalness of the fragrance.

What is claimed is:

1. A compound of formula:

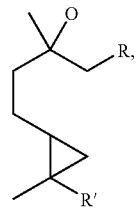

wherein R and R' each independently is selected from the group consisting of H, $CH_3$, $C_2H_5$, $C_3H_7$, $C_4H_9$, $C_5H_{11}$, $CH(CH_3)CH_2CH_2CH_3$, $CH_2CH(CH_3)CH_2CH_3$, $CH_2CH_2CH(CH_3)CH_3$, cyclopropyl, cyclobutyl, cyclopentyl, $CH=CHCH_2CH_2CH_3$, $CH_2CH=CHCH_2CH_3$, $CH_2CH_2CH=CHCH_3$, and $CH=C(CH_3)CH_2CH_3$.

2. The compound of claim 1, wherein R and R' each independently is a straight, branched, or cyclic hydrocarbon moiety consisting of less then 5 carbon atoms.

3. A compound of

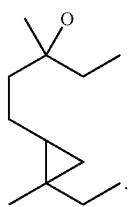

4. A method of improving, enhancing or modifying a fragrance formulation through the addition of an olfactory acceptable amount of a compound of formula:

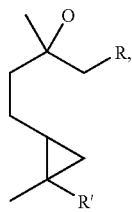

wherein R and R' each independently is selected from the group consisting of H, $CH_3$, $C_2H_5$, $C_3H_7$, $C_4H_9$, $C_5H_{11}$, $CH(CH_3)CH_2CH_2CH_3$, $CH_2CH(CH_3)CH_2CH_3$, $CH_2CH_2CH(CH_3)CH_3$, cyclopropyl, cyclobutyl, cyclopentyl, $CH=CHCH_2CH_2CH_3$, $CH_2CH=CHCH_2CH_3$, $CH_2CH_2CH=CHCH_3$, and $CH=C(CH_3)CH_2CH_3$.

5. The method of claim 4, wherein the compound is

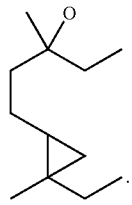

6. The method of claim 4, wherein the fragrance formulation is incorporated into a product selected from the group consisting of a perfume, a cologne, a toilet water, a cosmetic product, a personal care product, a fabric care product, a cleaning product, and an air freshener.

7. The method of claim 6, wherein the cleaning product is selected from the group consisting of a detergent, a dishwashing composition, a scrubbing compound, and a window cleaner.

8. The method of claim 4, wherein the olfactory acceptable amount is from about 0.005 to about 10 weight percent.

9. The method of claim 4, wherein the olfactory acceptable amount is from about 0.5 to about 8 weight percent.

10. The method of claim 4, wherein the olfactory acceptable amount is from about 1 to about 7 weight percent.

11. A fragrance formulation containing the compound of claim 1.

12. The fragrance formulation of claim 11, wherein the compound of claim 1 is:

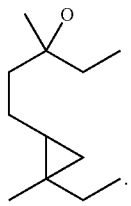

13. A fragrance product containing the compound of claim 1.

14. The fragrance product of claim 13, wherein the compound of claim 1 is:

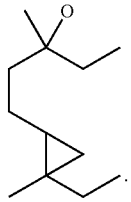

* * * * *